US00PP27163P3

(12) United States Plant Patent
Bell

(10) Patent No.: US PP27,163 P3
(45) Date of Patent: Sep. 20, 2016

(54) BLUEBERRY PLANT NAMED 'RIDLEY 4514'

(50) Latin Name: ***Vaccinium* hybrid**
Varietal Denomination: Ridley 4514

(71) Applicant: Mountain Blue Orchards Pty Ltd., Lindendale (AU)

(72) Inventor: Ridley Bell, Lindendale (AU)

(73) Assignee: Mountain Blue Orchards PTY LTD., Lindendale, NSW (AU)

( * ) Notice: Subject to any disclaimer, the term of this patent is extended or adjusted under 35 U.S.C. 154(b) by 67 days.

(21) Appl. No.: 14/544,546

(22) Filed: Jan. 20, 2015

(65) Prior Publication Data

US 2015/0216095 P1 Jul. 30, 2015

Related U.S. Application Data

(60) Provisional application No. 61/965,151, filed on Jan. 24, 2014.

(51) Int. Cl.
*A01H 5/08* (2006.01)

(52) U.S. Cl.
USPC ..... Plt./157

(58) Field of Classification Search
USPC ..... Plt./157
See application file for complete search history.

(56) References Cited

U.S. PATENT DOCUMENTS

PP20,695 P2 2/2010 Wright et al.

*Primary Examiner* — Annette Para
(74) *Attorney, Agent, or Firm* — Hahn Loeser & Parks, LLP

(57) ABSTRACT

The new blueberry plant variety 'Ridley 4514' is provided. 'Ridley 4514' is a commercial variety intended for the market. The variety is produced from a cross of seed parent 'C99-42' (U.S. Plant Pat. No. 20,695) with pollen parent 'C00-008' (unpatented), which can be distinguished by its outstanding features.

3 Drawing Sheets

Latin name of the family, genus, and species: Family—Ericaceae. Genus—*Vaccinium*. Species—hybrid.

Variety denomination: The new blueberry plant claimed is of the variety denominated 'Ridley 4514'.

BACKGROUND OF THE INVENTION

The present invention relates to a new and distinct perennial variety of *Vaccinium* hybrid (Southern Highbush Blueberry), which has been given the variety denomination of 'Ridley 4514. Its market class is that of a fruiting plant. 'Ridley 4514' is intended for use as fresh fruit for shipping, customer pick and processing markets and as a home garden plant.

The new *Vaccinium* hybrid cultivar is a selection resulting from seedlings produced in a breeding programme of *Vaccinium* at Lindendale, NSW, Australia in 2006 from the controlled pollination of seed parent 'C99-42' (U.S. Plant Pat. No. 20,695) with pollen parent 'C00-008' (unpatented). The new cultivar was discovered and selected as a single plant within a population of 100 resulting *Vaccinium* hybrid plants from this controlled pollination in 2008 in a commercial field plantation environment at Lindendale, New South Wales, Australia. Selection criteria was a combination of strong plant growth vigor, low chilling requirement, early time of flowering and fruit ripening, large to very large firm fruit suited to handling, high yield, desirable tasting berries and small picking scar.

The selection was subsequently evaluated for a number of years at the commercial farms at Lindendale, New South Wales, Australia.

Asexual reproduction of the new cultivar by cutting propagation since 2009 at Lindendale, New South Wales, Australia has demonstrated that the new cultivar reproduces true to type with all of the characteristics, as herein described, firmly fixed and retained through successive generations of such asexual propagation.

SUMMARY OF THE INVENTION

The new *Vaccinium* hybrid cultivar is a selection resulting from seedlings produced in a breeding programme of *Vaccinium* at Lindendale, NSW, Australia in 2006 from the controlled pollination of seed parent 'C99-42' (U.S. Plant Pat. No. 20,695) with pollen parent 'C00-008' (unpatented).

Plants of the new cultivar differ from plants of the seed parent 'C99-42' primarily in very strong plant growth vigor, large to very large berry diameter, very firm fruit firmness, high level of sweetness and very early flowering season whereas the seed parent has medium plant growth vigor, medium berry diameter, medium fruit firmness, medium level of sweetness and early-medium flowering season. Plants of the new cultivar differ from plants of the pollen parent 'C00-008' primarily in very strong plant growth vigor, large to very large berry diameter, very firm fruit firmness and very early flowering season whereas the pollen parent has strong plant growth vigor, large berry diameter, soft to medium fruit firmness and medium flowering season.

The new *Vaccinium* hybrid cultivar is a selection resulting from seedlings produced in a breeding programme of *Vaccinium* at Lindendale, NSW, Australia in 2006 from the controlled pollination of seed parent 'C99-42' (U.S. Plant Pat. No. 20,695) with pollen parent 'C00-008' (unpatented). The new cultivar was discovered and selected as a single plant within a population of 100 resulting *Vaccinium* hybrid plants from this controlled pollination in 2008 in a commercial field plantation environment at Lindendale, New South Wales, Australia. Selection criteria was a combination of strong plant growth vigor, low chilling requirement, early time of flowering and fruit ripening, large firm fruit suited to handling, high yield, desirable tasting berries and small picking scar.

The selection was subsequently evaluated for a number of years at the commercial farms at Lindendale, New South Wales, Australia.

The following characteristics of the new cultivar have been repeatedly observed and can be used to distinguish 'RIDLEY 4514' as a new and distinct cultivar of *Vaccinium* hybrid plant:

1. Upright plant growth habit
2. Very early timing of beginning of flowering
3. early timing of fruit ripening
4. Very strong plant growth vigor
5. Dark blue berry color
6. Berry firmness is very firm
7. Picking scar is dry
8. Leaf width is broad
9. Berry size is large to very large
10. Berry sweetness is medium to high Plants of the new cultivar differ from plants of the seed parent 'C99-42' primarily in very strong plant growth vigor, large to very large berry diameter, very firm fruit firmness, high level of sweetness and very early flowering season whereas the seed parent has medium plant growth vigor, medium berry diameter, medium fruit firmness, medium level of sweetness and early-medium flowering season. Plants of the new cultivar differ from plants of the pollen parent 'C00-008' primarily in very strong plant growth vigor, large to very large berry diameter, very firm fruit firmness and very early flowering season whereas the pollen parent has strong plant growth vigor, large berry diameter, soft to medium fruit firmness and medium flowering season.

Asexual reproduction of the new cultivar by cutting propagation since 2009 at Lindendale, New South Wales, Australia has demonstrated that the new cultivar reproduces true to type with all of the characteristics, as herein described, firmly fixed and retained through successive generations of such asexual propagation.

BRIEF DESCRIPTION OF THE DRAWINGS

The accompanying photographic illustration shows typical specimens in full color of the foliage and fruit of the new variety 'Ridley 4514.' The colors are as nearly true as is reasonably possible in a color representation of this type.

Figure 1:
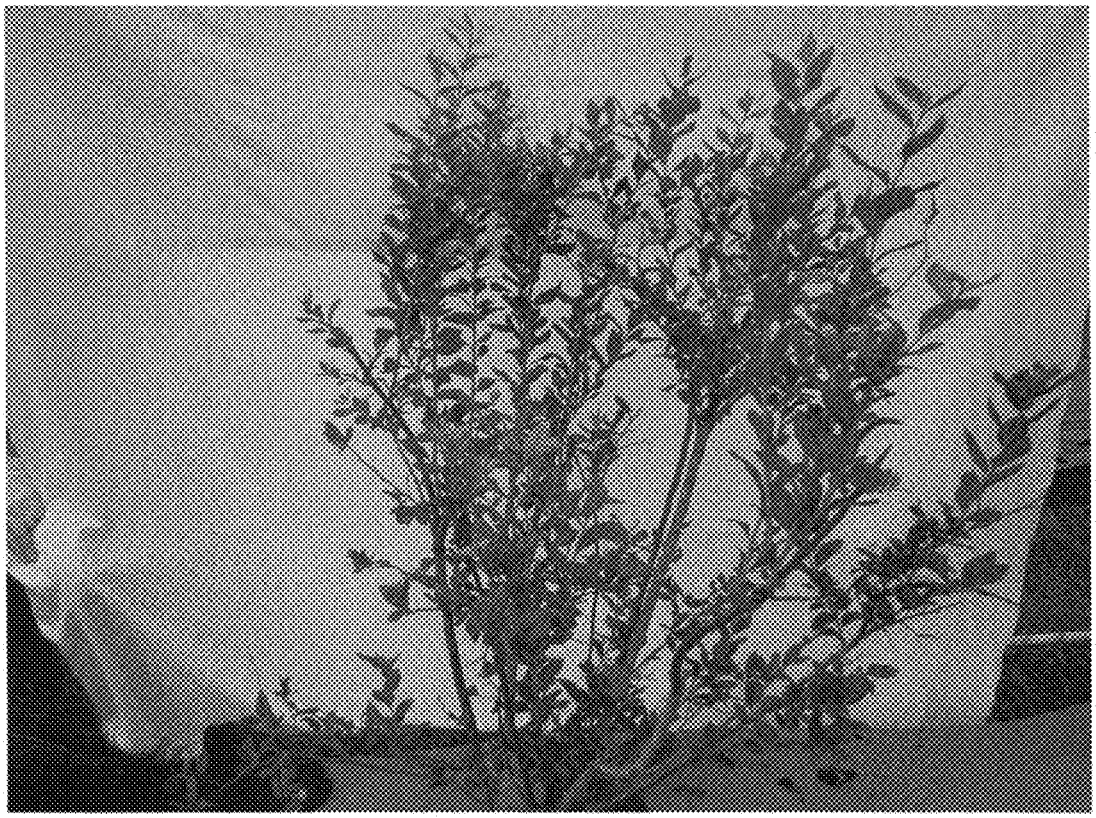
FIG. 1 is a photograph of the new variety 'Ridley 4514', demonstrating the plant's upright growth habit.
Figure 2:
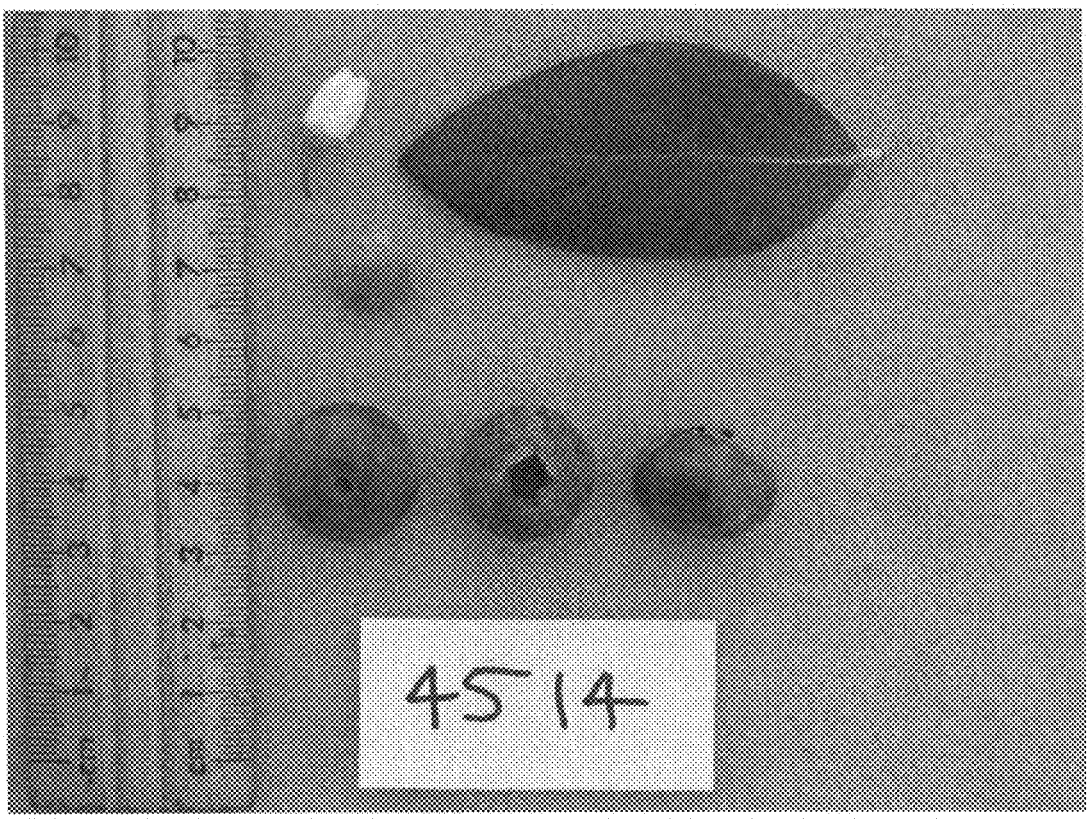
FIG. 2 is a photograph of the flower, leaf and fruit of the new variety 'Ridley 4514'.
Figure 3:
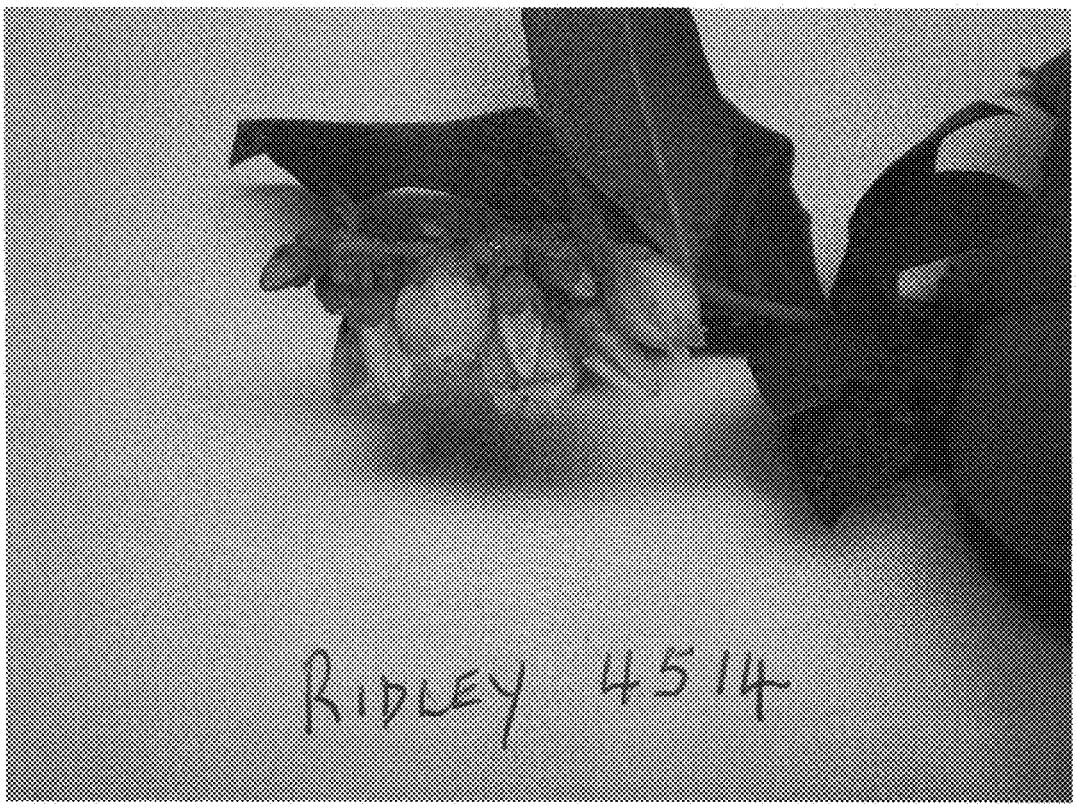
FIG. 3 is a photograph of the inflorescence of the new variety 'Ridley 4514.'

The colors in the photographs are as close as possible with the photographic and printing technology utilized. The color values cited in the detailed botanical description accurately describe the colors of the new blueberry.

DETAILED BOTANICAL DESCRIPTION

The following detailed description sets forth the distinctive characteristics of 'Ridley 4514'. The data which defines these characteristics was collected from asexual reproductions of the original selection. Dimensions, sizes, colors, and other characteristics are approximations and averages set forth as accurately as possible. The plant history was taken on plants approximately 4 years of age, and the descriptions relate to plants grown in the field in Lindendale, New South Wales, Australia. Descriptions of fruit characteristics were made on fruit grown in Lindendale, New South Wales, Australia. Color designations are from Lindendale, New South Wales, Australia.

Color notations are based on The Royal Horticultural Society Color Chart, of The Royal Horticultural Society, London, 2007 edition.

Classification:

*a. Family.*—Ericaceae.
*b. Genus.*—*Vaccinium.*
*c. Species.*—hybrid.
*d. Common name.*—Southern Highbush Blueberry.

Parentage:

*Female parent.*—'C99-42.' (U.S. Plant Pat. No. 20,695).
*Male parent.*—'C00-008.' (unpatented).

Market class: A fruiting plant intended for use as fresh fruit for shipping, customer pick and processing markets and as a home garden plant.

PLANT

General:

*Parentage.*—Female Parent — 'C99-42.' (U.S. Plant Pat. No. 20,695). Male Parent — 'C00-008.' (unpatented).
*Plant height.*—2.0 m.
*Plant width.*—1.2 m.
*Growth habit.*—Upright.
*Growth.*—Very strong vigor.
*Productivity.*—Greater than 5 kg per season from 3-4 year old plants planted at 3.0 m×0.9 m density.
*Cold hardiness.*—Has not been grown in all environments including harsh winter environments.
*Cold tolerance.*—Cold tolerance is expected to be low.
*Chilling requirement.*—Has not been grown in all environments and is typically grown as an evergreen crop where chilling hours are not important. 'Ridley 4514' is classed as 'low chill', typical of Southern Highbush Blueberry varieties with an estimated chilling requirement of 250 hours (not tested).
*Tolerance to disease.*—Moderate resistance to root disease (*phytophthora* spp) and good resistance to blueberry rust.
*Leafing.*—Vegetative bud burst is late when grown as an evergreen in Australia.
*Twigginess.*—Low.

STEM

General:

*Suckering tendency.*—Plants typically have 5-7 major canes per plant from a base 30 cm in diameter on 6 year old plants.
*Mature cane color.*—Color greyed orange 198C.
*Mature cane length.*—0.8-0.9 m.
*Mature cane width.*—1.2 cm.
*Bark texture.*—Medium roughness (typical of species).
*Surface texture of new wood.*—Smooth.
*Internode length on strong, new shoots.*—15-20 mm.
*Fruiting wood.*—To 15 cm in length.

FOLIAGE

General:

*Time of beginning of leaf bud burst.*—Late.
*Leaf color* (*top side*).—Yellow green 147A.

*Leaf color* (*under side*).—Yellow green 147C.
*Leaf arrangement.*—Alternate.
*Leaf shape.*—Elliptic.
*Leaf margins.*—Entire.
*Undulation of margin.*—Weak.
*Leaf venation.*—Reticulate.
*Leaf apices.*—Acuminate.
*Leaf bases.*—Obtuse.
*Leaf length.*—50-70 mm.
*Leaf width.*—28-34 mm.
*Leaf length/width ratio.*—Medium.
*Leaf nectarines.*—Absent.
*Pubescence of upper side.*—Absent.
*Pubescence of lower side.*—Absent.
*Cross sectional profile.*—Flat.
*Longitudinal profile.*—Straight.
*Attitude.*—Semi-upright to horizontal.

Petioles:
*Length.*—1.0 to 3.0 mm.
*Width.*—2.0 mm.
*Color.*—Yellow green 146C-147C.

FLOWERS

General:
*Time of beginning of flowering.*—Very early (late April to Early May at Lindendale, NSW Australia).
*Time of* 50% *anthesis.*—Early July at Lindendale, NSW Australia.
*Flower shape.*—Urceolate.
*Flower bud density.*—Medium density.
*Flower fragrance.*—Weak.

Corolla:
*Color.*—White NN155D.
*Length.*—15-16 mm.
*Width.*—9-10 mm.
*Aperture width.*—3-5 mm.
*Anthocyanin coloration of corolla.*—Absent.
*Corolla ridges.*—Present.
*Protrusion of stigma.*—Usually absent.

Inflorescence:
*Length.*—40 to 70 mm.
*Diameter.*—20-40 mm.
*Length of peduncle.*—15 mm.
*Surface texture of peduncle.*—Smooth.
*Color of peduncle.*—Yellow green 146C.
*Length of pedicel.*—8-10 mm.
*Surface texture of pedicel.*—Smooth.
*Color of pedicel.*—Yellow green 147C.
*Number of flowers per cluster.*—10-14.
*Flower cluster density.*—Medium.

Calyx (with sepals):
*Diameter.*—9-12 mm.
*Color* (*sepals*).—Green 138C to yellow green 147C.

Stamen:
*Length.*—4-5 mm.
*Number per flower.*—Approximately 10.
*Filament color.*—Yellow green 144D.

Pistil:
*Style.*—Length — 5-6 mm.
*Ovary color* (*exterior*).—Yellow green 144D-yellow green 147C.

Anther:
*Length.*—3.0-3.5 mm.
*Number.*—Approximately 10.
*Color.*—Grayed orange 167C-D.

Pollen:
*Abundance.*—Medium.
*Color.*—Grayed orange 167C-D.
*Self-compatibility.*—60% fruit set with own pollen in tests at Lindendale, NSW Australia.

FRUIT

General:
*Time of fruit ripening.*—Early (Early July at Lindendale, NSW Australia).
*Time of* 50% *maturity.*—Mid-late September.
*Fruit development period.*—55 days.
*Cluster density.*—Dense, 8-10 berries per cluster.
*Unripe fruit color.*—Green 138A.
*Ripe berry color.*—Black 202A.
*Berry surface wax abundance.*—Strong.
*Berry flesh color.*—Grayed green 194A-195A.
*Berry weight.*—2.5-3.0 g.
*Berry height from calyx to scar.*—12-14 mm.
*Berry diameter.*—20 mm.
*Berry shape.*—Oblate.
*Fruit stem scar.*—Small (dry).
*Sweetness when ripe.*—Medium to high.
*Firmness when ripe.*—Firm.
*Acidity when ripe.*—Weak.
*Storage quality.*—Good, lasted 10 weeks at 2 degrees Celsius in tests. Not tested with modified atmosphere storage yet.
*Suitability for mechanical harvesting.*—Upright plant habit and very firm fruit firmness, strong blush and fruit shape suited to mechanical harvesting. Shake requirement and season compactness not yet tested.
*Self-fruitfulness.*—60% fruit set with own pollen in tests at Lindendale, NSW Australia.
*Uses.*—Fresh fruit for shipping, customer pick and processing markets and as a home garden plant.

SEED

General:
*Seed abundance in fruit.*—Abundant.
*Seed color.*—Greyed orange 174B.
*Seed length.*—1.6-1.8 mm.

COMPARISON BETWEEN PARENTAL AND COMMERCIAL CULTIVARS

| Organ | Context | Ridley4514 | Ridley 3402 | Ridley 0501 | C99-42 | C00-008 |
|---|---|---|---|---|---|---|
| Plant | vigour | Strong to very strong | strong | medium | medium to strong | strong |
| Plant | growth habit | upright | semi-upright | upright to semi-upright | semi-upright | semi-upright |
| One-year-old shoot | colour | green | green | green | green | green |

-continued

COMPARISON BETWEEN PARENTAL AND COMMERCIAL CULTIVARS

| Organ | Context | Ridley4514 | Ridley 3402 | Ridley 0501 | C99-42 | C00-008 |
|---|---|---|---|---|---|---|
| One-year-old shoot | length of internode | medium | medium | medium | medium | medium |
| long to very Leaf | long to very length | medium to long | medium to long | long | Tong | long |
| medium to Leaf | medium to width | medium to broad | broad to very broad | broad | broad | broad |
| Leaf | shape | elliptic | elliptic | elliptic | elliptic | elliptic |
| Leaf | colour of upper side | green | green | green | green | green |
| Leaf | intensity of green colour on upper side | medium | medium | light to medium | medium | dark |
| Leaf | margin | entire | entire | entire | entire | entire |
| Flower bud | anthocyanin coloration | weak | weak | weak | weak | weak |
| Flower | shape of corolla | urceolate | urceolate | urceolate | urceolate | urceolate |
| Flower | size of corolla tube | medium | small to medium | medium | medium | medium |
| Flower | anthocyanin colouration of corolla tube | absent or very weak | absent or very weak | absent or very weak | weak to medium | absent or very weak |
| Flower | ridges on corolla tube | present | present | present | present | present |
| medium to Fruit cluster | density | medium | medium | dense | dense | dense |
| Unripe fruit | intensity of green colour | light | light | light | light | light |
| Fruit | size | large to very large | medium | medium | large | large |
| Fruit | shape in longitudinal section | oblate | oblate | round | round | round |
| Fruit | attitude of sepals | erect | erect | erect | erect | erect |
| Fruit | diameter of calyx basin | medium to large | medium to medium | small to large | medium | medium |
| Fruit | depth of calyx basin | medium to deep | deep to very deep | deep | deep | deep |
| Fruit | intensity of bloom | weak to strong | strong | medium | medium | medium |
| Fruit | colour of skin | dark blue | dark blue | dark blue | dark blue | dark blue |
| Fruit | firmness | firm | soft to medium | medium to firm | medium | soft to medium |
| Fruit | sweetness | medium to high | medium to high | low to medium | medium | medium to high |
| Fruit | acidity | weak | medium to high | medium to high | low to medium | low |
| Time of | vegetative bud burst | late | medium | medium | early | medium |
| Time of | beginning of flowering | early to very early | early | very early | medium | medium |
| Time of | beginning of fruit ripening | early to early | early to medium | early to medium | medium | medium to late |

The invention claimed is:

1. A new and distinct variety of blueberry plant named 'Ridley 4514', substantially as illustrated and described herein.

* * * * *